United States Patent
Cheng et al.

(10) Patent No.: US 7,396,545 B2
(45) Date of Patent: Jul. 8, 2008

(54) PREPARATION FOR CARDIO-CEREBRAL BLOOD VESSEL DISEASES AND ITS PREPARING METHOD

(75) Inventors: Yiyu Cheng, Tianjin (CN); Haijiang Zhang, Tianjin (CN); Zhengliang Ye, Tianjin (CN)

(73) Assignee: Tianjin Tasly Pharmaceutical Co., Ltd., Tianjin (CN)

( * ) Notice: Subject to any disclaimer, the term of this patent is extended or adjusted under 35 U.S.C. 154(b) by 0 days.

(21) Appl. No.: 11/522,296

(22) Filed: Sep. 15, 2006

(65) Prior Publication Data

US 2007/0071834 A1    Mar. 29, 2007

Related U.S. Application Data

(63) Continuation of application No. PCT/CN2005/000333, filed on Mar. 17, 2005.

(30) Foreign Application Priority Data

Mar. 17, 2004    (CN) ................... 2004 1 0018758

(51) Int. Cl.
*A61K 36/254* (2006.01)
*A61K 36/258* (2006.01)

(52) U.S. Cl. ..................................... 424/728

(58) Field of Classification Search .................... None
See application file for complete search history.

(56) References Cited

U.S. PATENT DOCUMENTS

2005/0037094 A1* 2/2005 Yan et al. ..................... 424/728

OTHER PUBLICATIONS

Li, Lian-Niang, Water Soluble Active COmponents of *Salvia miltiorrhiza* and Related Plants, 1997, 6(2), 57-64.*

* cited by examiner

*Primary Examiner*—Susan Hoffman
*Assistant Examiner*—Catheryne Chen
(74) *Attorney, Agent, or Firm*—Schwegman, Lundberg & Woessner P.A.

(57) ABSTRACT

The present invention discloses a traditional Chinese medicine preparation for cardio-cerebral blood vessel diseases, it is prepared through extracting danshen and *Notoginseng* by lye, precipitating with alcohol, concentrating, and adding other medicine and excipients. Then using the HAPLY-MS and HAPLY fingerprint Atlas to characterize its Physicochemical properties completely. Using the fingerprint Atlas analysis method of the present invention, the structure and comparative content of biologically active component can be known. Characterization of the physical chemical properties of danshen and *Notoginseng* of traditional Chinese medicine preparation with this way is better than other methods of the prior art.

12 Claims, 3 Drawing Sheets

PREPARATION FOR CARDIO-CEREBRAL BLOOD VESSEL DISEASES AND ITS PREPARING METHOD

RELATED APPLICATIONS

This application is a continuation under 35 U.S.C. 111(a) of PCT/CN2005/000333, filed Mar. 17, 2005 and published as WO 2005/087242 A1, filed Sep. 22, 2005, which claimed priority under 35 U.S.C. 119 to Chinese Application No. 200410018758.4, filed Mar. 17, 2004, which applications and publication are incorporated herein by reference and made a part hereof.

TECHNICAL FIELD

The invention relates to a medicine, and in particular, to a traditional Chinese medicine preparation for the treatment of cardiovascular and cerebrovascular diseases.

BACKGROUND ART

Cardiovascular and cerebrovascular diseases are common ones which do great harm to health of human beings. Recently, such diseases have an increasing occurrence due to the changes of works, livings, diet patterns, environments and the like with social development. The traditional Chinese medicine (TCM), in spite of its lower activity toward a single target relative to the Western medicine, is characterized by its multiple routes and targets, dynamic and holistic treatment, and low side effects, which are far beyond the effects of the Western medicine. The TCM preparation with definite therapeutic effect will have an overall therapeutic effect superior to that of the Western medicine. There have been now a plurality of TCM preparations for the treatment of cardiovascular and cerebrovascular diseases, such as compound Danshen tablets and its TCM preparations, Guanxin Danshen drop pills, and Xinkeshu tablets etc. These TCM preparations, all of which contain *Radix Salviae Miltiorrhizae* (also known as danshen) and *Radix Notoginseng*, have different therapeutic effects for their different formulations, proportions of ingredients, extraction and purification processes, or dosage forms. In addition, these TCM preparations can hardly be controlled in quality, since no effective quality detection method is available at present for completely characterizing the physical and chemical properties of these medicines, and instead, only one or two compounds, such as Danshensu or Tanshinone IIA, are used to represent the complex biologically active ingredients in these medicines. Therefore, it is necessary to improve the process for extracting and purifying such TCM preparations and also the method for controlling their qualities.

SUMMARY OF THE INVENTION

It is an object of the present invention to provide a more effective TCM preparation for the treatment of cardiovascular and cerebrovascular diseases. Also provided herein is a detection method for relatively complete and exact characterization of the physical and chemical properties thereof.

It is another object of the present invention to provide a process for preparing the above TCM preparation.

The objects of the present invention are achieved through the following embodiments.

The TCM preparation according to the present invention can be prepared through a process comprising the following steps of:

mixing *Radix Salviae Miltiorrhizae* and *Radix Notoginseng* with sodium hydroxide, sodium bicarbonate, sodium carbonate, potassium hydroxide, potassium bicarbonate, potassium carbonate or a mixture thereof in an amount of 0.5%-4.0% based on the total weight of said medicinal materials to obtain a mixture;

boiling the mixture out in 3-6 folds of water for 2-4 times;

subjecting the mixture to filtration and concentrating the combined filtrates;

adding an ethanol with a high concentration (above 70%) in an amount sufficient to obtain a 65-70% content of the ethanol;

allowing the mixture to stand and separating the supernatant; recovering the ethanol from the supernatant and concentrating the residue until it has a relative density of 1.20-1.50 (55-60° C.), which is an extract of *Radix Salviae Miltiorrhizae-Radix Notoginseng*;

mixing the above extract with Borneol (or an oil of *Lignum Dalbergiae Odoriferae*); and adding one or more pharmacological excipients, such as starch, dextrin, lactose, microcrystalline cellulose, hydroxypropyl methyl cellulose, polyethylene glycol, magnesium stearate, micro silicon gel, xylitol, lactitol, glucose, glycine, mannitol, methyl starch sodium, cross-linked sodium carboxyl methyl cellulose, cross-linked polyvinylpyrrolidone etc., to formulate the mixture into various dosage forms, such as injection, tablet, sustained-release tablet, drop pill, granule, injection powder, capsule, microgranule, oral disintegrant.

Preferably, the above TCM preparation is prepared through a process comprising the following steps of:

weighing *Radix Salviae Miltiorrhizae* and *Radix Notoginseng*;

adding sodium bicarbonate in an amount of 1.4%-1.9% based on the total weight of said medicinal materials to obtain a mixture;

boiling the mixture out in 4-5 folds of water for 2-3 hours, and then in 3-4 folds of water for another 1-2 hours;

subjecting the mixture to filtration and concentrating the combined filtrates until a specific gravity of 1.16-1.20 (80±5° C.) is achieved;

adding an ethanol with a high concentration (above 70%) in an amount sufficient to obtain a 65-70% content (20° C. of the ethanol;

allowing the mixture to stand for 8-12 hours and separating the supernatant;

recovering the ethanol from the supernatant and concentrating the residue until it has a relative density of 1.32-1.40 (55-60° C.), which is an extract of *Radix Salviae Miltiorrhizae-Radix Notoginseng*; mixing the above extract with Borneol (or an oil of *Lignum Dalbergiae Odoriferae*); and adding one or more pharmacological excipients selected from the group consisting of starch, dextrin, lactose, microcrystalline cellulose, hydroxypropyl methyl cellulose, polyethylene glycol, magnesium stearate, micro silicon gel, xylitol, lactitol, glucose, glycine, mannitol, methyl starch sodium, cross-linked sodium carboxyl methyl cellulose, cross-linked polyvinylpyrrolidone etc. to formulate the mixture into tablet, drop pill, injection powder, capsule, granule, microgranule, or oral disintegrant.

The Borneol used herein can be a naturally occurring or synthesized one. The oil of *Lignum Dalbergiae Odoriferae* used herein is obtained through distillation of *Lignum Dalbergiae Odoriferae*.

The above TCM preparation is preferably in the dosage form of drop pill.

The TCM preparation according to the present invention is characterized using the following physical and chemical parameters:

in the HPLC spectrum, there are 8 peaks which have a ratio of single peak area to total peak area greater than 2%; the average retention time of these 8 peaks is 6.04, 9.90, 16.89, 17.84, 20.31, 23.74, 27.73 and 31.02 respectively, and the RSD % of the retention time is 0.31, 0.25, 0.61, 0.70, 0.96, 0.76, 0.50 and 1.18 respectively; their average peak area is 1627.92, 2575.54. 366.89, 381.40, 186.08, 555.35, 281.91 and 1852.33 respectively, and the RSD % of the peak area is 5.91, 13.53, 10.92, 13.81, 12.04, 10.48, 18.08 and 14.84 respectively; and the ratio of single peak area to total peak area accounts for 19.6%-22.0%, 28.5%-37.4%, 4.2%-5.2%, 4.2%-5.5%, 2.1%-2.7%, 6.4%-7.8%, 3.0%-4.3% and 20.2%-27.2% respectively.

The above physical and chemical parameters were obtained under the following detection conditions:

(1) High Performance Liquid Chromatography Octadecyl-silyl-silica gel was used as a filler for the chromatography column, with flow rate of 1.000 ml/min and detection wavelength of 280 nm. The Elution was carried out under the following conditions: mobile phase A being a 0.02% aqueous phosphoric acid solution, mobile phase B being a 80% acetonitrile-0.02% aqueous phosphoric acid solution, mobile phase A being changed from 90% to 78% homogeneously and mobile phase B being changed from 10% to 22% homogeneously during 0 to 8 min; mobile phase A from 78% to 74% and mobile phase B from 22% to 26% during 8 to 15 min; and mobile phase A from 74% to 48% and mobile phase B from 26% to 52% during 15 to 55 min.

(2) Preparation and Determination of Sample Solution

10 pills of the TCM preparation according to the present invention are weighed accurately, and then, added into a 10 ml measuring bottle. Distilled water was added in an amount sufficient to dissolve the pills through shaking with ultrasound for 15 minutes. And more distilled water was then added to achieve a volume of 10 ml. The resultant solution was subjected to centrifugation or filtration to obtain a sample solution. An accurate 10 μl of the sample solution was injected into a HPLC apparatus, and then determined by way of HPLC chromatography to obtain a HPLC spectrum.

Figure 1:
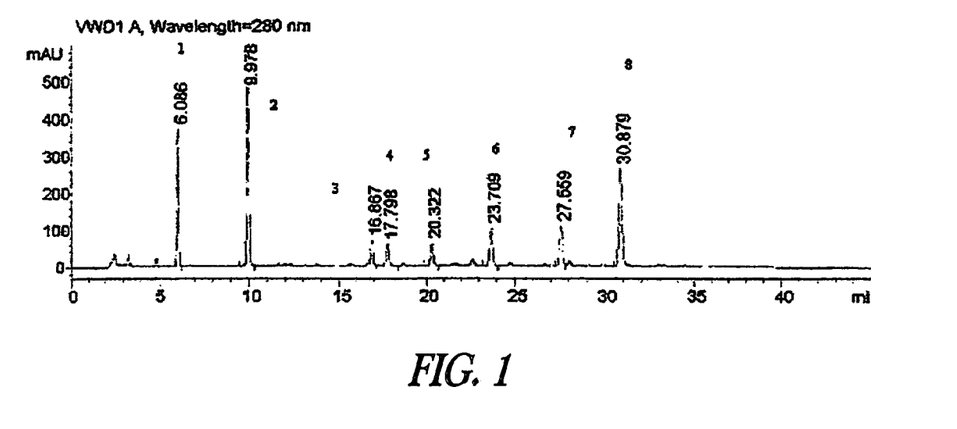
FIG. 1 is a fingerprint atlas of the components of the *Radix Salviae Miltiorrhizae* in the drop pills as one of the dosage forms of the present TCM preparation. In this figure, peak 1 represents Danshensu; peak 2 represents Protocatechualdehyde; peak 3 represents Isolithospermic acid A; peak 4 represents Isolithospermic acid B; peak 5 represents Salvianolic acid D; peak 6 represents Rosmarinic acid; peak 7 represents Salvianolic acid B; and peak 8 represents Salvianolic acid A.

With the aid of an analysis method, such as a comparison with a standard sample and Mass Spectra, the above 8 peaks with an average retention time of 6.04, 9.90, 16.89, 17.84, 20.31, 23.74, 27.73 and 31.02 were identified to correspond with Danshensu, Protocatechualdehyde, Isolithospermic acid A, Isolithospermic acid B, Salvianolic acid D, Rosmarinic acid, Salvianolic acid B and Salvianolic acid A, respectively (see FIG. 1).

Using a particular HPLC-MS method, the TCM preparation of the present invention was determined to comprise Danshensu, Protocatechualdehyde, Isolithospermic acid A, Isolithospermic acid B, Salvianolic acid D, Salvianolic acid E, Rosmarinic acid, Salvianolic acid B, Salvianolic acid G, Salvianolic acid A, Tanshinone I, Tanshinone II A, Notoginsenoside $R_1$, Ginsenoside Re, Ginsenoside Rg1, Ginsenoside Rb1, Notoginsenoside R2, Notoginsenoside R2 iso., Ginsenoside Rg2, Ginsenoside Rh1, Ginsenoside Rh1 iso., Ginsenoside Rd, Ginsenoside Rd iso., Ginsenoside Rf-H2O, Notoginsenoside R2-H2O, Ginsenoside Rg6 or F4, Ginsenoside Rk3, Ginsenoside (Rh4), Ginsenoside 20(R)-Rg3, Ginsenoside 20(S)-Rg3, Ginsenoside (Rk1), Ginsenoside (Rg5) and the like.

-continued

9

10

11

| | | |
|---|---|---|
| 1. Danshensu | MW = 198 |
| 2. Protocatechualdehyde | MW = 138 |
| 3. Salvianolic acid A | MW = 494 |
| 4. Salvianolic acid B | MW = 718 |
| 5. Salvianolic acid C | MW = 492 |
| 6. Salvianolic acid D | MW = 418 |
| 7. Salvianolic acid E | MW = 718 |
| 8. Salvianolic acid G | MW = 340 |
| 9. Isolithospermic acid A | MW = 538 |
| 10. Isolithospermic acid B | MW = 538 |
| 11. Rosmarinic acid | MW = 360 |

Type A

-continued

Type B

Type C

Type D

| Structure Type A | | | |
|---|---|---|---|
| Ginsenoside | $R_1$ | $R_2$ | Molecular Weight (MW) |
| Ginsenoside $Rb_1$ | Glc-Glc | Glc-Glc | 1108 |
| Ginsenoside Rd | Glc-Glc | Glc | 946 |
| Ginsenoside $Rg_3$ | Glc-Glc | H | 784 |
| Ginsenoside $F_2$ | Glc | Glc | 784 |

| Structure Type B | | | | |
|---|---|---|---|---|
| Ginsenoside | $R_1$ | $R_2$ | $R_3$ | MW |
| Ginsenoside Re | H | Glc | O-Glc-Rham | 946 |
| Ginsenoside Rf | H | H | O-Glc-Glc | 800 |
| Ginsenoside $Rg_1$ | H | Glc | O-Glc | 800 |
| Ginsenoside $Rg_2$ | H | H | O-Glc-Rham | 784 |
| Ginsenoside $Rh_1$ | H | H | O-Glc | 638 |
| Notoginsenoside $R_2$ | H | H | O-Glc-Xyl | 770 |
| Notoginsenoside $R_1$ | H | Glc | O-Glc-Xyl | 932 |
| Ginsenoside $F_1$ | H | Glc | OH | 638 |

| Structure Type C | | | |
|---|---|---|---|
| Ginsenoside | $R_1$ | $R_2$ | MW |
| Ginsenoside $Rg_5$ | Glc-Glc- | H | 766 |
| Ginsenoside $Rh_4$ | H | Glc-O— | 620 |
| Ginsenoside $F_4$ | H | Rham-Glc-O— | 766 |

-continued

Structure Type D

| Ginsenoside | $R_1$ | $R_2$ | MW |
|---|---|---|---|
| Ginsenoside $Rg_6$ | H | Rham-Glc-O— | 766 |
| Ginsenoside $Rk_1$ | Glc-Glc | H | 766 |
| Ginsenoside $Rk_3$ | H | Glc-O— | 620 |

Glc = β-D-glucose
Rham = α-L-rhamnose
Xyl = β-D-xylose

In the extraction process and analysis method of the present invention, fingerprint atlas was used for completely characterizing the physical and chemical properties of the *Radix Salviae Miltiorrhizae* and the *Radix Notoginseng* in the TCM preparation. Compared to the prior art in which only one or two compounds are used to represent complex biologically active ingredients in TCM preparations, this characterization means is more suitable for controlling the quality of the TCM preparations.

The biologically active ingredients in the present TCM preparations were detected using the HPLC-MS analysis method according to the present invention. As a result, 12 components from *Radix Salviae Miltiorrhizae* and 21 components from *Radix Notoginseng* have been identified in total. The compounds were identified mainly based on an analysis of the $MS^n$ data and comparison with data from literature. Finally, a large number of the components were completely confirmed with respect to their structures through comparison with the control samples. It can be concluded thereby that the analysis for the chemical composition of the present TCM preparation using the HPLC-MS method of the present invention can produce abundant information on the structure of the biologically active ingredients. The characterization by these information for the physical and chemical properties of *Radix Salviae Miltiorrhizae* and *Radix Notoginseng* in the present TCM preparation has consequently a much better effect than those methods in the prior art.

The following tests demonstrate that the present TCM preparation has an effect on the treatment of cardiovascular and cerebrovascular diseases.

1. Effects of the TCM Preparation on Myocardial Ischemia and Myocardial Infarction in Anaesthetized Dog An epicardial electrogram was used to map a range of myocardial ischemia and to indicate the extent thereof. Quantitative histology (N-BT staining method) was used to determine an area of myocardial infarction. Also determined were changes of blood flow of coronary artery, myocardial oxygen consumption, and activities of serum CK and LDH, and blood plasma ET, $TXB_2$, and 6-Keto-$PGF_{1\alpha}$. The TCM preparation according to the present invention was studied upon alimentary administration with regard to its effect on acute myocardial ischemia, myocardial infarction, and related indicators in test dogs.

The test results show that the TCM preparation according to the present invention has a significant effect in improving acute myocardial ischemia and myocardial infarction of dogs. It can lead to a reduced extent of myocardial ischemia (Σ-ST) indicated by the epicardial electrogram (P<0.001 relative to the control group using normal saline), a significantly reduced area of infarction indicated through N-ST staining (P<0.001 relative to the control group using normal saline), and a significantly increased blood flow of coronary artery in an ischemic heart (P<0.001 relative to the control group using normal saline). It has an inhibitory action against the release of serum lactate dehydrogenase (LDH) resulted from myocardial ischemia and myocardial infarction (with a relative change ratio significantly lower than that of the control group using normal saline, P<0.001), as well as against the increase of the activity of creatine phosphokinase (CK) (with a relative change ratio significantly lower than that of the control group using normal saline, P<0.05). It has also an effect in reducing blood plasma ET (P<0.001 relative to the control group using normal saline) and $TXB_2$ level (P<0.001 relative to the control group using normal saline, P<0.05 relative to the group using a TCM preparation) of blood plasma, and improving the ratio of 6-Keto-$PGF_{1\alpha}$/$TXB_2$ (P<0.001 relative to the control group using normal saline, P<0.05 relative to the group using a TCM preparation).

2. Effects of the TCM Preparation on Myocardial Infarction Caused by Ischemic Reperfusion It was found through an observation on a rat model with the damage of myocardial ischemia reperfusion that, the TCM preparation according to the present invention could lead to a significantly reduced extent of myocardial damage, a decreased area of myocardial infarction (p<0.05-0.01 relative to the model group), and a less weight of an infarction part (p<0.05 relative to the model group). It has also an effect in significantly increasing the activity of superoxide dismutase (SOD) (p<0.01 relative to the model group).

3. Effects of the TCM Preparation on Dynamics of Cardiac Blood Flow and Myocardial Oxygen Consumption in Dogs The TCM preparation of the present invention was evaluated with respect to its effect on dynamics of cardiac blood flow and myocardial oxygen consumption in anaesthetized normal dogs.

The results show that the TCM preparation according to the present invention can lead to a significantly improved blood flow of coronary artery (p<0.01-0.001 relative to the group before administration and the control group using normal saline), an expanded coronary vessel, an increased oxygen content in coronary vein sinus (p<0.05-0.001 relative to the group before administration and the control group using normal saline), a reduced myocardial oxygen consumption indicator, an improved supply of blood and oxygen to cardiac muscle, and an increased output per heartbeat and cardiac output (p<0.05-0.01 relative to the group before administration and the control group using normal saline) without enhancing left ventricular work. The present TCM preparation has also an effect in adjusting cardiac complaisance, and thus, in adapting and improving a cardiovascular system.

4. Effects of the TCM Preparation on Platelet Agglutination in Rabbits

The TCM preparation of the present invention was evaluated through Born nephelometry with respect to its effect on platelet agglutination in rabbits.

The results show that the TCM preparation can, upon an intragastric administration for 7 successive days, lead to a significant reduction of the platelet agglutination in rabbits induced by arachidonic acid (AA) (p<0.05-0.01 relative to the control group using distilled water) and collagen (p<0.01 relative to the control group using distilled water). This indicates that the TCM preparation according to the present invention has an inhibitory effect on platelet agglutination.

5. Effects of the TCM Preparation on Thrombogenesis in Vitro and Blood Viscosity in Rats The TCM preparation of the present invention was evaluated with respect to its effect on thrombogenesis in vitro and blood viscosity in rats.

The results show that the TCM preparation can, upon an intragastric administration for 7 successive days, lead to a considerably shortened thrombus (p<0.01 relative to the control group using distilled water), a decreased wet and dry weight of the thrombus (p<0.05 relative to the control group using distilled water), a reduced viscosity of blood plasma (p<0.001 relative to the control group using distilled water), and a decreased whole blood viscosity at various shear rates (p<0.05 relative to the control group using distilled water). This indicates that the TCM preparation according to the present invention has an effect in inhibiting thrombogenesis, and reducing viscosity of blood plasma and of whole blood.

6. Effects of the TCM Preparation on Hyperlipidemia and Atherosclerosis in Rabbits A hyperlipidemia and atherosclerosis (AS) model for test was established through feeding fodder with a high content of cholesterol to a rabbit. The TCM preparation of the present invention was evaluated with respect to its effect on this model.

The results show that the TCM preparation according to the present invention can lead to a significantly decreased concentration of TC, TG, LDL-C, VLDL-C in serum and a decreased TC/HDL-C ratio (p<0.05-0.001 relative to the control group suffering from Hyperlipidemia) in rabbits, a significantly increased HDL-C concentration (p<0.05 relative to the control group suffering from Hyperlipidemia), a decreased content of TC in the aorta (p<0.05 relative to the control group suffering from Hyperlipidemia), a decreased content of TG in the liver (p<0.05 relative to the control group suffering from Hyperlipidemia), and a decreased content of MDA in the liver (p<0.001 relative to the control group suffering from Hyperlipidemia). The present TCM preparation has a significant effect in improving the activity of SOD in the liver (p<0.01 relative to the control group suffering from Hyperlipidemia). Furthermore, it has a significant effect in reducing the thickness of aorta plaque and the amount of the foam cells formed in the aorta (p<0.05 relative to the control group suffering from Hyperlipidemia). It also leads to a decreasing tendency of the area of the aorta plaque. These indicate that the TCM preparation according to the present invention has an effect in adjusting blood fat, and at the same time, a certain effect of the anti-peroxidation of lipid and prevention of arteriosclerosis.

7. Effects of the TCM Preparation on Localized Cerebral Ischemia in Rats

Using a rat model with a middle cerebral artery thrombosis (MCAT), the TCM preparation of the present invention was determined with respect to its effect on an area of cerebral infarction in MCAT rats.

The results demonstrate that the TCM preparation according to the present invention has a significant effect of anti-cerebral ischemia.

DETAILED DESCRIPTION OF THE EMBODIMENTS

The invention will be further illustrated in details by reference to the following examples. The examples are for illustrative purpose and are not intended to limit the scope of the invention.

EXAMPLES

Example 1

Preparation Example 41.06 g of *Radix Salviae Miltiorrhizae* and 8.03 g of *Radix Notoginseng* were weighed out, to which sodium bicarbonate was added in an amount of 1.8% based on the total weight of said medicinal materials. The resulting mixture was boiled out in 4 folds of water for 2 hours, and then in 3 folds of water for another 1 hour. After filtration, the combined filtrates were concentrated until a specific gravity of 1.19-1.20 (75±1° C.) was achieved. Then, a 95% ethanol was added in an amount sufficient to obtain a 65% content of the ethanol (20° C.). The mixture was subsequently allowed to stand for 12 hours, and the supernatant was separated. The ethanol was recovered from the supernatant, and the residue was concentrated until it had a relative density of 1.37 (55-60° C.), which was an extract of *Radix Salviae Miltiorrhizae-Radix Notoginseng*.

The above extract was then mixed uniformly with 0.46 g of Borneol and 18 g of polyethylene glycol-6000. The mixture was melted at a temperature of 85° C. for 80 mins. The melting liquor was then introduced into the dropping tank of a drop-pill machine with the tank temperature being maintained at 86° C., in which the liquor was dropped into a liquid paraffin at 8° C. The obtained drop pills were taken out, subjected to an oil removal and then screened through a sieve to obtain the desired preparation.

Example 2

Preparation Example 59.36 g of *Radix Salviae Miltiorrhizae* and 6.38 g of *Radix Notoginseng* were weighed out, to which potassium carbonate was added in an amount of 1.0% based on the total weight of said medicinal materials. The resulting mixture was boiled out in 4 folds of water for 2.5 hours, and then in 3 folds of water for another 1.5 hours. After filtration, the combined filtrates were concentrated until a specific gravity of 1.19-1.20 (75±1° C.) was achieved. Then, a 85% ethanol was added in an amount sufficient to obtain a 70% content of the ethanol (20° C.). The mixture was subsequently allowed to stand for 10 hours, and the supernatant was separated. The ethanol was recovered from the supernatant, and the residue was concentrated until it had a relative density of 1.35 (55-60° C. ), which was an extract of *Radix Salviae Miltiorrhizae-Radix Notoginseng*.

The above extract was then mixed uniformly with 0.34 g of Borneol and 23 g of polyethylene glycol-6000. The mixture was melted at a temperature of 89° C. for 100 mins. The melting liquor was then introduced into the dropping tank of a drop-pill machine with the tank temperature being maintained at 85° C., in which the liquor was dropped into a methyl silicone oil at 8° C. The obtained drop pills were taken out, subjected to an oil removal and then screened through a sieve to obtain the desired preparation.

Example 3

Preparation Example 12.60 g of *Radix Salviae Miltiorrhizae* and 56.15 g of *Radix Notoginseng* were weighed out, to which potassium bicarbonate was added in an amount of 1.0% based on the total weight of said medicinal materials. The resulting mixture was boiled out in 4 folds of water for 2.5 hours, and then in 3 folds of water for another 1.5 hours. After filtration, the combined filtrates were concentrated until a specific gravity of 1.19-1.20 (75±1° C.) was achieved. Then, a 95% ethanol was added in an amount sufficient to obtain a 70% content of the ethanol (20° C.). The mixture was subsequently allowed to stand for 10 hours, and the supernatant was separated. The ethanol was recovered from the supernatant, and the residue was concentrated until it had a relative density of 1.35 (55-60° C.), which was an extract of *Radix Salviae Miltiorrhizae-Radix Notoginseng*.

The above extract was then mixed with 0.34 g of Borneol and 23 g of polyethylene glycol-6000. The mixture was melted at a temperature of 89° C. for 100 mins. The melting liquor was then introduced into the dropping tank of a drop-pill machine with the tank temperature being maintained at 85° C., in which the liquor was dropped into a methyl silicone oil at 8° C. The obtained drop pills were taken out, subjected to an oil removal and then screened through a sieve to obtain the desired preparation.

Example 4

Preparation Example 31.12 g of *Radix Salviae Miltiorrhizae* and 9.21 g of *Radix Notoginseng* were weighed out, to which sodium hydroxide was added in an amount of 0.5% based on the total weight of said medicinal materials. The resulting mixture was boiled out in 4 folds of water for 1.5 hours, and then in 3 folds of water for another 1.5 hour. After filtration, the combined filtrates were concentrated until a specific gravity of 1.19-1.20 (75±1° C.) was achieved. Then, a 88% ethanol was added in an amount sufficient to obtain a 66% content of the ethanol (20° C.). The mixture was subsequently allowed to stand for 10 hours, and the supernatant was separated. The ethanol was recovered from the supernatant, and the residue was concentrated until it had a relative density of 1.40 (55-60° C. ), which was an extract of *Radix Salviae Miltiorrhizae-Radix Notoginseng*.

The above extract was then mixed uniformly with 0.50 g of Borneol, 90 g of mannitol, 15 g of calciumedetate sodium and 15 ml of distilled water. The resultant mixture was lyophilized, and finally formulated into injection powders.

Example 5

Preparation Example 116.35 g of *Radix Salviae Miltiorrhizae* and 58.21 g of *Radix Notoginseng* were weighed out, to which sodium bicarbonate was added in an amount of 2.0% based on the total weight of said medicinal materials. The resulting mixture was boiled out in 4 folds of water for 2 hours, and then in 3 folds of water for 1.5 hour. After filtration, the combined filtrates were concentrated until a specific gravity of 1.19-1.20 (75±1° C.) was achieved. Then, a 88% ethanol was added in an amount sufficient to obtain a 66% content of the ethanol (20° C.). The mixture was subsequently allowed to stand for 10 hours, and the supernatant was separated. The ethanol was recovered from the supernatant, and the residue was concentrated until it had a relative density of 1.40 (55-60° C. ), which was an extract of *Radix Salviae Miltiorrhizae-Radix Notoginseng*.

The above extract was then mixed uniformly with 1.80 g oil of *Lignum Dalbergiae Odoriferae* and 40 g of microcrystalline cellulose. A 3% solution of polyvidone in ethanol was added to soften the mass. The softened mass was then sieved through an 18-size mesh to form granules. The granules were dried at a temperature of 60° C. for 35 mins, trimmed, and then mixed uniformly with 4 g of talcum powders. The mixture obtained was encapsulated to obtain the desired preparation.

Example 6

Preparation Example 116.35 g of *Radix Salviae Miltiorrhizae* and 58.21 g of *Radix Notoginseng* were weighed out, to which sodium bicarbonate was added in an amount of 2.0% based on the total weight of said medicinal materials. The resulting mixture was boiled out in 4 folds of water for 2 hours, and then in 3 folds of water for 1.5 hour. After filtration, the combined filtrates were concentrated until a specific gravity of 1.19-1.20 (75±1° C.) was achieved. Then, a 88% ethanol was added in an amount sufficient to obtain a 66% content of the ethanol (20° C.). The mixture was subsequently allowed to stand for 10 hours, and the supernatant was separated. The ethanol was recovered from the supernatant, and the residue was concentrated until it had a relative density of 1.40 (55-60° C. ), which was an extract of *Radix Salviae Miltiorrhizae-Radix Notoginseng*.

The above extract was then mixed uniformly with 0.90 g of Borneol, 120 g of microcrystalline cellulose, 40 g of hydroxypropyl methyl cellulose, 5 g of xylitol, and 2 g of magnesium stearate. The obtained mixture was compressed into tablets to obtain the desired preparation.

Example 7

Preparation Example 140.35 g of *Radix Salviae Miltiorrhizae* and 36.42 g of *Radix Notoginseng* were weighed out, to which sodium bicarbonate was added in an amount of 2.5% based on the total weight of said medicinal materials. The resulting mixture was boiled out in 4 folds of water for 2 hours, and then in 3 folds of water for 1.5 hour. After filtration, the combined filtrates were concentrated until a specific gravity of 1.19-1.20 (75±1° C.) was achieved. Then, a 90% ethanol was added in an amount sufficient to obtain a 65% content of the ethanol (20°

C.). The mixture was subsequently allowed to stand for 8 hours, and the supernatant was separated. The ethanol was recovered from the supernatant, and the residue was concentrated until it had a relative density of 1.35 (55-60° C.), which was an extract of *Radix Salviae Miltiorrhizae-Radix Notoginseng*.

The above extract was then mixed uniformly with 1.00 g of Borneol and 46 g of microcrystalline cellulose. A 3% solution of polyvidone in ethanol was added to soften the mass. The softened mass was then sieved through an 18-size mesh to form granules. The granules were dried at a temperature of 60° C. for 30 mins, trimmed, and then mixed uniformly with 4 g of talcum powders. The mixture obtained was compressed into tablets to obtain the desired preparation.

Example 8

Detection Example for Active Component

1. Preparation of Sample (1) The Water-Soluble Components of the *Radix Salviae Miltiorrhizae* in the Present TCM Preparation 148.4 mg was weighed out each for the TCM drop pills from example 1, 2 and 3, the TCM injection powders from example 4, the TCM capsules from example 5, the TCM oral disintegrant tablets from example 6, and the TCM tablets from example 7. Said preparations were dissolved in 6 ml of water through ultrasound for 15 mins, and then filtered through a 0.45 μm nylon film to obtain a yellow sample solution, respectively.

(2) The Components of the *Radix Notoginseng* and Liposoluble Components of the *Radix Salviae Miltiorrhizae* in the Present TCM Preparation 1003.8 mg was weighed out each for the TCM drop pills from example 1, 2 and 3, the TCM injection powders from example 4, the TCM capsules from example 5, the TCM oral disintegrant tablets from example 6, and the TCM tablets from example 7. Said preparations were dissolved in 10 ml of 4% aqueous ammonia through ultrasound for 15 mins, and then filtered through a 0.45 μm nylon film, respectively. The filtrate was pretreated on an Extract-Clean $C_{18}$ (Alltech Associates, Inc, U.S.) column. This sample, upon loaded into the column, was washed with 10 ml of water, and then eluted with 2 ml of methanol to obtain the test sample as a yellow eluent, respectively.

2. Analysis of Sample (1) Instruments and Agents

Agilent Series-1100 Liquid Chromatograph (Agilent); G1315A Diode Array Detector G1313A Automatic Sample Injector; G1316A Thermostat; G1322A Deaerator and Duplex Pump; HP Instrument Chromatographic Work Station.

Type G2445A Series 1100 LC-MSD/Trap Mass Spectrograph (Bruker); Ionization was carried out by means of electro-spraying; Extract-Clean $C_{18}$ Column(100 mg/ml, Alltech Associates, Inc, U.S.), acetonitrile being chromatographically pure (TEDIA), water being redistilled water, and acetic acid being analytically pure.

(2) Detection Conditions of Instruments

Agilent Zorbax SB-C18 chromatographic column (5 μm, 4.6 mm×25 cm, Agilent, SN USCL009296) was used for HPLC analysis. The gradient elution and mass spectrum detection of each sample were performed under following conditions.

① The Water-soluble Components of the *Radix Salviae Miltiorrhizae* in the TCM Preparation from Each Example HPLC Elution Conditions:

| time (min) | mobile phase A (%) | mobile phase B (%) |
|---|---|---|
| 0 | 95.0 | 5.0 |
| 15 | 78.3 | 21.7 |
| 33 | 78.3 | 21.7 |
| 38 | 65.0 | 35.0 | mobile phase A: acetic acid:water = 0.01:100
mobile phase B: acetic acid:acetonitrile = 0.01:100
flow rate: 0.5 ml/min
temperature: 30° C.
detection wavelength: multiple wavelength (280 nm of indicated wavelength)

MS Analysis Conditions:

| Ion detection manner | HPLC-MS | HPLC-MS$^n$ |
|---|---|---|
| | negative ion detection | |
| Dry gas flow rate (L/min) | 10 | 10 |
| Nebulizer pressure (psi) | 60 | 60 |
| Dry temperature (° C.) | 350 | 350 |
| Capillary voltage (v) | 3500 | 3500 |
| Mass scan range (m/z) | 100-1200 | 100-800 |
| Fragment amplitude (ev) | | 1.5-3.0 |

② The components of the *Radix Notoginseng* in the TCM Preparation from Each Example HPLC Elution Conditions:

| time (min) | mobile phase A (%) | mobile phase B (%) |
|---|---|---|
| 0 | 80 | 20 |
| 15 | 65 | 35 |
| 25 | 65 | 35 |
| 40 | 57 | 43 |
| 50 | 54 | 46 |
| 65 | 42 | 58 |
| 75 | 25 | 75 | mobile phase A: acetic acid:water = 0.01:100
mobile phase B: acetic acid:acetonitrile = 0.01:100
flow rate: 0.8 ml/min
temperature: 30° C.
detection wavelength: multiple wavelength (203 nm of indicated wavelength)

MS Analysis Conditions:

| Ion detection manner | HPLC-MS | HPLC-MS$^n$ |
|---|---|---|
| | negative ion detection | |
| Dry gas flow rate (L/min) | 10 | 10 |
| Nebulizer pressure(psi) | 60 | 60 |
| Dry temperature (° C.) | 350 | 350 |
| Capillary voltage (v) | 3500 | 3500 |
| Mass scan range (m/z) | 400-1500 | 400-1200 |
| Fragment amplitude (ev) | | 1.2-1.5 |

3. Analysis Results and Peak Identification

The components were identified in the following two aspects: (1) using control samples; (2) using the UV absorption properties and ion fragment information from MS$^n$ in combination with literature data

Figure 2:
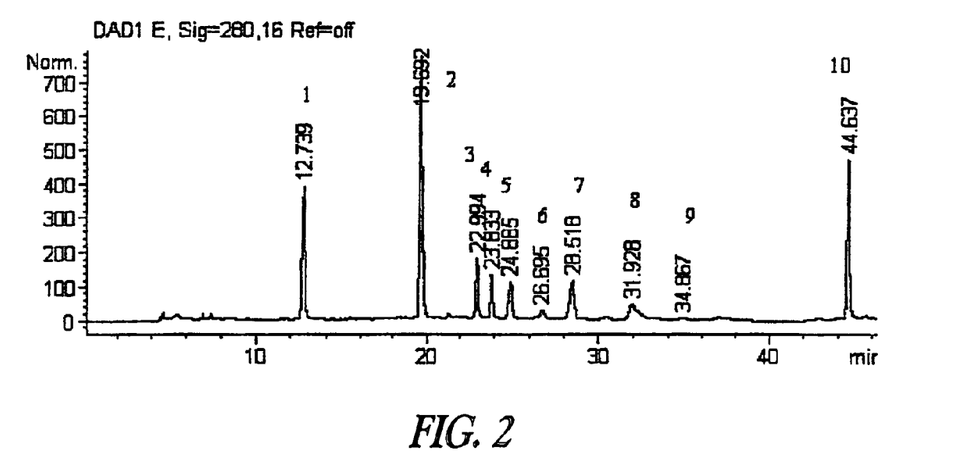
FIG. 2 is a HPLC spectrum of the water-soluble components of the *Radix Salviae Miltiorrhizae* in the present TCM preparation. In this figure, peak 1 represents Danshensu; peak 2 represents Protocatechualdehyde; peak 3 represents Isolithospermic acid A; peak 4 represents Isolithospermic acid B; peak 5 represents Salvianolic acid D; peak 6 represents Salvianolic acid E; peak 7 represents Rosmarinic acid; peak 8 represents Salvianolic acid B; peak 9 represents Salvianolic acid G; and peak 10 represents Salvianolic acid A.
Figure 3:
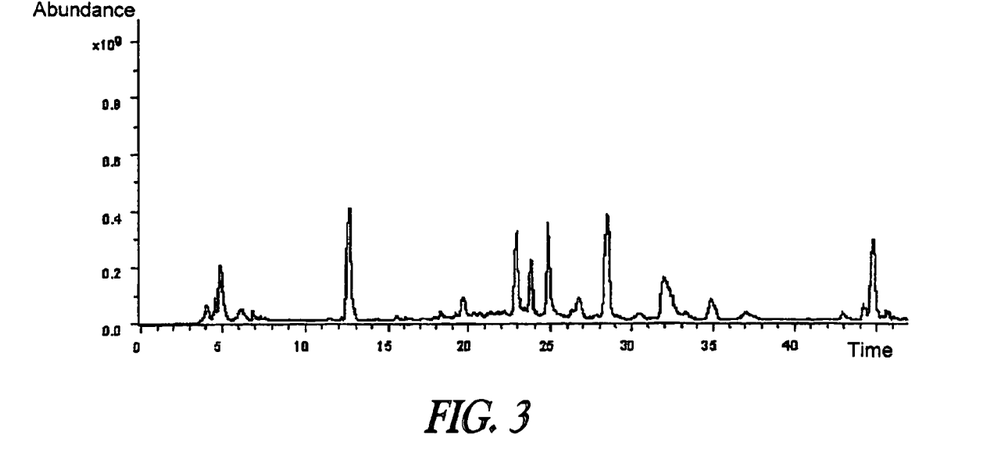
FIG. 3 is a MS-TIC spectrum of the water-soluble components of the *Radix Salviae Miltiorrhizae* in the present TCM preparation.

4. Identification Results (1) The Water-soluble Components of the *Radix Salviae Miltiorrhizae* in the *Radix Salviae Miltiorrhizae* Preparation from Each Example of the Present Invention (see tables 1 and 2, and FIGS. 2 and 3).

TABLE 1

HPLC-MS Data and Identification Results

| Peak No. | Retention Time | Quasi-Molecular Ion Mass Peak m/z [M−H]⁻ | Identity | Max. Absorption Wavelength λmax |
|---|---|---|---|---|
| 1 | 12.73 | 197 | Danshensu | 280 |
| 2 | 19.69 | 137 | Protocatechual-dehyde | 231, 280, 310 |
| 3 | 22.99 | 537 | Isolithospermic acid A | 327 |
| 4 | 23.83 | 537 | Isolithospermic acid B | 327 |
| 5 | 24.89 | 417 | Salvianolic acid D | 247, 321 |
| 6 | 26.70 | 717 | Salvianolic acid E | 330 |
| 7 | 28.51 | 359 | Rosmarinic acid | 329 |
| 8 | 31.93 | 717 | Salvianolic acid B | 254, 286, 309 |
| 9 | 34.86 | 339 | Salvianolic acid G | 395 |
| 10 | 44.64 | 493 | Salvianolic acid A | 288 |

TABLE 2

HPLC-MS$^n$ Data

| Peak No. | Identity | Fragment ion m/z |
|---|---|---|
| 3 | Isolithospermic acid A | Second(537): 493[M-H—CO$_2$]⁻, 295[M-CO$_2$—R—H$_2$O]⁻ Third (295): 159, 109 |
| 4 | Isolithospermic acid B | Second (537): 493[M-H—CO$_2$]⁻, 295[M-CO$_2$—R—H$_2$O]⁻ Third (295): 159, 109 |
| 5 | Salvianolic acid D | Second (417): 175[M-CO$_2$—R—H$_2$O]⁻, 373[M-H—CO$_2$]⁻ Third (175): 147, 157, 133 |
| 6 | Salvianolic acid E | Second (717): 519[M-R—H$_2$O]⁻, 321[M-2R—2H$_2$O]⁻ Third (519): 321[M-R—H$_2$O]⁻, 339[M-R]⁻ Third (321): 279, 293, 249, 223, 185 |
| 7 | Rosmarinic acid | Second (359): 161[M-R—H$_2$O]⁻, 179[M-R]⁻, 195 |
| 8 | Salvianolic acid B | Second (717): 519[M-R—H$_2$O]⁻, 321[M-2R—2H$_2$O]⁻ Third (519): 321[M-R—H$_2$O]⁻, 339[M-R]⁻ Fourth (321): 279, 293, 249, 233, 185 |
| 9 | Salvianolic acid G | Second (339): 321[M-H—H$_2$O]⁻, 295[M-H—CO$_2$]⁻ Third (295): 279, 267 Fourth (279): 251 |
| 10 | Salvianolic acid A | Second (493): 295[M-R—H$_2$O]⁻ Third (295): 159, 109 | it can be seen from the MS$^n$ results that the second and third peak have very similar structures as that of lithospermic acid. They are considerably different from lithospermic acid, however, with respect to UV absorption. Lithospermic acid has a relatively strong absorption near 253 nm due to its phenyl coumaran backbone, while the second and third peak do not have such a absorption property. Both of these peaks have UV absorption very similar with that of Salvianolic acid E, which demonstrates that the two compounds corresponding to these two peaks are likely to have the same backbone as Salvianolic acid E, i.e. the structure of carboxyl diphenyl ethylene backbone. It is thereby concluded that they have structures as those of Isolithospermic acids A and B shown in the above structure formula for components.

These two structures have never been reported, and are therefore named as Isolithospermic acids A and B herein.

Figure 4:
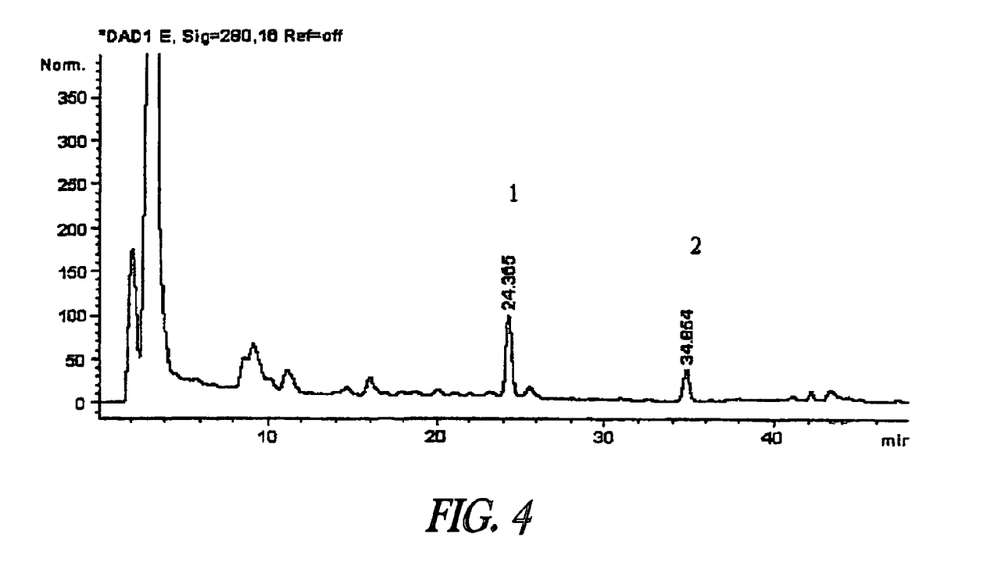
FIG. 4 is a HPLC spectrum of the liposoluble components of the *Radix Salviae Miltiorrhizae* in the present TCM preparation. In this figure, peak 1 represents Tanshinonel; and peak 2 represents Tanshinone IIA.
Figure 5:
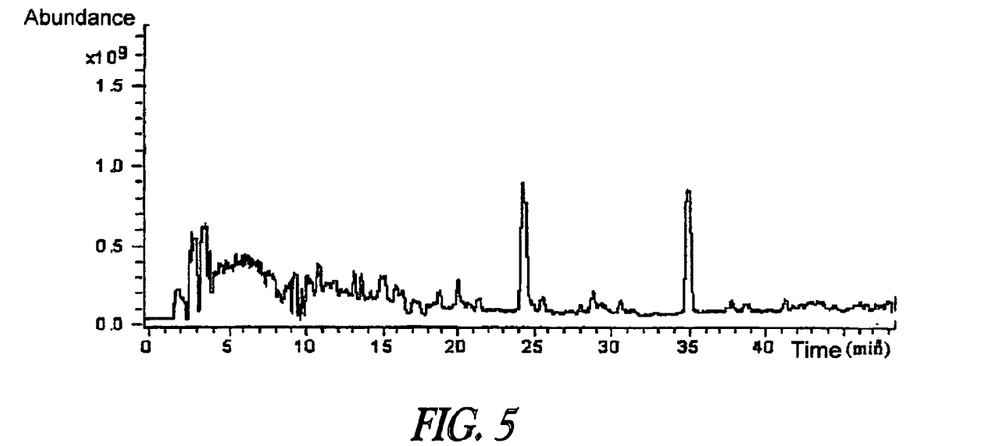
FIG. 5 is a MS-TIC spectrum of the liposoluble components of the *Radix Salviae Miltiorrhizae* in the present TCM preparation.

(2) The Liposoluble Components of the *Radix Salviae Miltiorrhizae* in the TCM Preparation of the Present Invention (see table 3, and FIGS. 4 and 5).

TABLE 3

HPLC-MS Data and Identification Results

| Peak No. | Retention Time | Quasi-Molecular Ion Mass Peak m/z⁻ | Identity |
|---|---|---|---|
| 1 | 24.36 | 277 [M + H]⁺, 575 [2M + Na]⁺ | Tanshinone I |
| 2 | 34.85 | 295 [M + H]⁺, 611 [2M + Na]⁺ | Tanshinone IIA |

Figure 6:
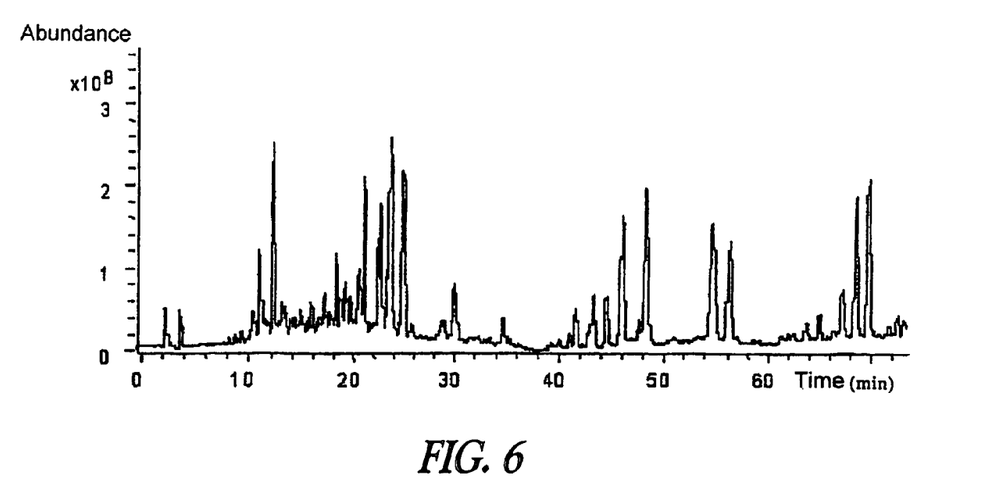
FIG. 6 is a MS-TIC spectrum of the components of the *Radix Notoginseng* in the present TCM preparation.

(3) The Components of the *Radix Notoginseng* in the *Radix Salviae Miltiorrhizae* Drop Pills of the Present Invention (see tables 4 and 5, and FIG. 6).

TABLE 4

HPLC-MS Data and Identification Results

| Peak No. | Retention Time | Quasi-Molecular Ion Mass Peak m/z [M-H]⁻ | Identity |
|---|---|---|---|
| 1 | 11.27 | 931 | Notoginsenoside R$_1$ |
| 2 | 12.38 | 945 | Ginsenoside Re |
| 2 | 12.53 | 799 | Ginsenoside Rg$_1$ |
| 3 | 20.81 | 1107 | Ginsenoside Rb$_1$ |
| 4 | 21.25 | 769 | Notoginsenoside R$_2$ |
| 5 | 22.53 | 769 | Notoginsenoside R$_2$ iso. |
| 6 | 22.85 | 783 | Ginsenoside Rg$_2$ |
| 7 | 23.77 | 637 | Ginsenoside Rh$_1$ |
| 8 | 25.00 | 637 | Ginsenoside Rh$_1$ iso. (F$_1$) |
| 9 | 30.05 | 945 | Ginsenoside Rd |
| 10 | 34.81 | 945 | Ginsenoside Rd iso. |
| 11 | 40.00 | 781 | Ginsenoside Rf-H$_2$O |
| 12 | 41.57 | 751 | Notoginsenoside R$_2$—H$_2$O |
| 13 | 43.72 | 751 | Notoginsenoside R$_2$—H$_2$O |
| 14 | 44.89 | 765 | Ginsenoside Rg$_6$/F$_4$ |
| 15 | 46.43 | 619 | Ginsenoside Rk$_3$/Rh$_4$ (Rk$_3$) |
| 16 | 48.68 | 619 | Ginsenoside Rk$_3$/Rh$_4$ (Rh$_4$) |
| 17 | 54.97 | 783 | Ginsenoside 20(R)Rg$_3$ |
| 18 | 56.48 | 783 | Ginsenoside 20(S)Rg$_3$ |
| 19 | 68.35 | 765 | Ginsenoside Rk$_1$/Rg$_5$ (Rk$_1$) |
| 20 | 69.53 | 765 | Ginsenoside Rk$_1$/Rg$_5$ (Rg$_5$) |

TABLE 5

HPLC-MS$^n$ Data

| Retention Time | Identity | Quasi-Molecular Ion Mass Peak m/z⁻ |
|---|---|---|
| 11.27 | Notoginsenoside R$_1$ | 799[M-H-Xyl]⁻; 637[M-H-Xyl-Glc]⁻; 475[M-H-Xyl-2Glc]⁻ |
| 12.38 | Ginsenoside Re | 799[M-H-Rham]⁻; 783[M-H-Glc]⁻; 637[M-H-Rham-Glc]⁻; 475[M-H-Rham-2Glc]⁻ |
| 12.53 | Ginsenoside Rg$_1$ | 637[M-H-Glc]⁻; 475[M-H-2Glc]⁻ |
| 20.81 | Ginsenoside Rb$_1$ | 945[M-H-Glc]⁻; 783[M-H-2Glc]⁻; 621[M-H-3Glc]⁻; 459[M-H-4Glc]⁻ |

TABLE 5-continued

HPLC-MS$^n$ Data

| Retention Time | Identity | Quasi-Molecular Ion Mass Peak m/z$^-$ |
|---|---|---|
| 21.25 | Notoginsenoside R$_2$ | 637[M-H-Xyl]$^-$; 475[M-H-Xyl-Glc]$^-$ |
| 22.53 | Notoginsenoside R$_2$ iso. | 637[M-H-Xyl]$^-$; 475[M-H-Xyl-Glc]$^-$ |
| 22.85 | Ginsenoside Rg$_2$ | 637[M-H-Rham]$^-$; 475[M-H-Rham-Glc]$^-$ |
| 23.77 | Ginsenoside Rh$_1$ | 475[M-H-Glc]$^-$ |
| 25.00 | Ginsenoside Rh$_1$ iso. (F$_1$) | 475[M-H-Glc]$^-$ |
| 30.05 | Ginsenoside Rd | 783[M-H-Glc]$^-$; 621[M-H-2Glc]$^-$; 459[M-H-3Glc]$^-$ |
| 34.81 | Ginsenoside Rd iso. | 783[M-H-Glc]$^-$; 621[M-H-2Glc]$^-$; 459[M-H-3Glc]$^-$ |
| 40.00 | Ginsenoside Rf-H$_2$O | 619[M-H-Glc]$^-$; 457[M-H-2Glc]$^-$ |
| 41.57 | Notoginsenoside R$_2$—H$_2$O | 619[M-H-Xyl]$^-$ |
| 43.72 | Notoginsenoside R$_2$—H$_2$O | 619[M-H-Xyl]$^-$ |
| 44.89 | Ginsenoside Rg$_6$/F$_4$ | 619[M-H-Rham]$^-$; 457[M-H-Rham-Glc]$^-$ |
| 54.97 | Ginsenoside 20(R)Rg$_3$ | 621[M-H-Glc]$^-$; 459[M-H-2Glc]$^-$ |
| 56.48 | Ginsenoside 20(S)Rg$_3$ | 621[M-H-Glc]$^-$; 459[M-H-2Glc]$^-$ |
| 68.35 | Ginsenoside Rk$_1$/Rg$_5$ (Rk$_1$) | 603[M-H-Glc]$^-$; 441[M-H-2Glc]$^-$ |
| 69.53 | Ginsenoside Rk$_1$/Rg$_5$ (Rg$_5$) | 603[M-H-Glc]$^-$; 441[M-H-2Glc]$^-$ |

Based on the above research, the extraction process and analysis method for the TCM preparation of the present invention are established, which include:

(1) A Solid-Phase Process for Extracting the Liposoluble Components of *Radix Salviae Miltiorrhizae* and the Components of Notoginsenoside from the Drop Pills of *Radix Salviae Miltiorrhizae*;

(2) a Method of HPLC-MS Analysis for Each Sample 12 components from *Radix Salviae Miltiorrhizae* and 21 saponin components from *Radix Notoginseng* have been identified in total. Among them, 4 water-soluble components of *Radix Salviae Miltiorrhizae*, 2 liposoluble components of *Radix Salviae Miltiorrhizae* and 9 components of saponin have been identified through comparison with the control samples, while other compounds were identified mainly based on an analysis of MS$^n$ data and comparison with data from literature.

Example 9

Detection Example of the Fingerprint Atlas for the Components of *Radix Salviae Miltiorrhizae* in the TCM Preparation 1. Instruments and Agents Instruments: Agilent 1100 Liquid Chromatograph, comprising: quad-pump, online deaerating system, automatic sample injector, DAD detector, column temperature tank, Chemstation work station; BS210S electronic balance (1/10$^{-4}$ g) (Beijing Sartorius Company), METTLER AE240 electronic balance ((1/10$^{-4}$ g or 1/10$^{-5}$ g) (Mettler-Toledo Corporation, Shanghai), LD4-2 centrifuge (4000 r/min) (Beijing Medical Centrifuge Factory), Digital thermostatic water-bath kettle (Tianjing Changfeng Corporation), RE-52AA rotary evaporator (Shanghai Yarong Biochemical Instrumentation Factory), SHE-(III) water-circulating vacuum pump (Gongyi Yingyuyuhua Instrumentation Factory), KQ-250B ultrasonic cleanser (Kunshan Ultrasonic Instrumentation Corporation), HENGAO T&D filter(HENGGAO T&D), synthetic fiber membrane filter (aperture 0.45 μm)(Shanghai Xingya Purifying Materials Factory).

Agents: acetonitrile (chromatographically pure, Merck Company, US), phosphoric acid (top grade), Wahaha pure water.

2. Preparation of Test Sample 10 pills of the TCM preparation from each batch of Example 1 were weighed accurately and then introduced into a 10 ml measuring bottle. Distilled water was added to in an amount sufficient to dissolve the pills through shaking with ultrasound for 15 mins. And more distilled water was then added to achieve a volume of 10 ml. The obtained solution was subjected to centrifugation or filtration to obtain a sample solution.

3. HPLC Analysis Conditions

Agilent ZoRBAx SB-C18 (4.6×250 mm, 5 μm) chromatographic column; Mobile phase: mobile phase A being a 0.02% aqueous phosphoric acid solution, mobile phase B being a 80% acetonitrile-0.02% aqueous phosphoric acid solution; flow rate: 1.000 ml/min; detection wavelength: 280 nm, column temperature: 30° C.; injected sample volume: 10 μl.

Elution Gradient of Mobile Phase:

| Retention time | Mobile Phase A(v/v) | Mobile Phase B(v/v) |
|---|---|---|
| 0 min | 90% | 10% |
| 8 min | 78% | 22% |
| 15 min | 74% | 26% |
| 55 min | 48% | 52% |

4. Detection Results (see table 7)

TABLE 7

Detection Results for Components of *Radix Salviae Miltiorrhizae* in 200 Batches of Above TCM Drop Pills

| Peak No. | Average Retention Time | RSD % of Retention Time | Average Peak Area | RSD % of Peak Area | Percentage of Single Peak Area to Total Peak Area | Percentage Range of Single Peak Area to Total Peak Area |
|---|---|---|---|---|---|---|
| 1 | 6.04 | 0.31 | 1627.92 | 5.91 | 20.80% | 19.6%-22.0% |
| 2 | 9.90 | 0.25 | 2575.54 | 13.53 | 32.90% | 28.5%-37.4% |
| 3 | 16.89 | 0.61 | 366.89 | 10.92 | 4.69% | 4.2%-5.2% |

TABLE 7-continued

Detection Results for Components of *Radix Salviae Miltiorrhizae* in 200 Batches of Above TCM Drop Pills

| Peak No. | Average Retention Time | RSD % of Retention Time | Average Peak Area | RSD % of Peak Area | Percentage of Single Peak Area to Total Peak Area | Percentage Range of Single Peak Area to Total Peak Area |
|---|---|---|---|---|---|---|
| 4 | 17.84 | 0.70 | 381.40 | 13.81 | 4.87% | 4.2%-5.5% |
| 5 | 20.31 | 0.96 | 186.08 | 12.04 | 2.38% | 2.1%-2.7% |
| 6 | 23.74 | 0.76 | 555.35 | 10.48 | 7.09% | 6.4%-7.8% |
| 7 | 27.73 | 0.50 | 281.91 | 18.08 | 3.60% | 3.0%-4.3% |
| 8 | 31.02 | 1.18 | 1852.33 | 14.84 | 23.66% | 20.2%-27.2% |

Note:
Peak 1 represents Danshensu; peak 2 represents Protocatechualdehyde; peak 3 represents Isolithospermic acid A; peak 4 represents Isolithospermic acid B; peak 5 represents Salvianolic acid D; peak 6 represents Rosmarinic acid; peak 7 represents Salvianolic acid B; and peak 8 represents Salvianolic acid A (see FIG. 1).

Table 7 shows the relative positions and ratios of area (retention time and peak area) of 8 peaks, wherein 3 peaks have a ratio of single peak area to total peak area greater than 10% and all the 8 peaks have a ratio of single peak area to total peak area greater than 2%.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A preparation for the treatment of cardiovascular and cerebrovascular diseases, characterized in that it comprises two components both having a quasi-molecular ion mass peak m/z of 537[M-H]$^-$, a second fragment ion m/z of 493 [M-H-CO$_2$]$^-$ and 295[M-CO$_2$-R-H$_2$O]$^-$, and a third fragment ion m/z of 159 and 109, with the maximum absorption wave length of 327 nm, wherein the mass spectrum analysis is carried out as follows:
(1) HPLC-MS is carried out through the negative ion detection under following conditions of dry gas flow rate: 10 L/min; nebulizer pressure: 60 psi; dry gas temperature: 350° C.; capillary voltage: 3500 v; and m/z scan range: 100-1200; and
(2) HPLC-MS$^n$ is carried out through the negative ion detection under following conditions of dry gas flow rate: 10 L/min; nebulizer pressure: 60 psi; dry gas temperature: 350° C.; capillary voltage: 3500 v; m/z scan range: 100-800; and fragment amplitude: 1.5-3.0 v.

2. The preparation according to claim 1, characterized in that it comprises Isolithospermic acids A and B.

3. The preparation according to claim 1 characterized in that it comprises the components having a quasi molecular ion mass peak m/z of 417, 717, 359, 717, 339, and 493 [M-H]$^-$ respectively, wherein
the component with 417 [M-H]$^-$ has a second fragment ion m/z of 175[M-CO$_2$-R-H$_2$O]$^-$ and 373[M-H-CO$_2$]$^-$, and a third fragment ion m/z of 147, 157 and 133;
the component with 717[M-H]$^-$ has a second fragment ion m/z of 519[M-R-H$_2$O]$^-$ and 321[M-2R-2H$_2$O]$^-$, a third fragment ion m/z of 321 [M-R-H$_2$O]and 339[M-R]$^-$, and a third fragment ion m/z of 279, 293, 249, 223 and 185;
the component with 359 [M-H]$^-$ has a second fragment ion m/z of 161[M-R-H$_2$O]$^-$, 179[M-R]$^-$, and 195;
the component with 717 [M-H]$^-$ has a second fragment ion m/z of 519[M-R-H$_2$O]$^-$ and 321[M-2R-2H$_2$]$^-$, a third fragment ion m/z of 321 [M-R-H$_2$] and 339[M-R]$^-$, and a forth fragment ion m/z of 279, 293, 249, 233 and 185;
the component with 339 [M-H]$^-$ has a second fragment ion m/z of 321[M-H-H$_2$O]$^-$ and 295[M-H-CO$_2$]$^-$, a third fragment ion mz of 279 and 267, and a forth fragment ion m/z of 251; and
the component with 493 [M-H]$^-$ has a second fragment ion m/z of 295[M-R-H$_2$O]$^-$, and a third fragment ion m/z of 159 and 109;
wherein the mass spectrum analysis is carried out as follows:
(1) HPLC-MS is carried out through the negative ion detection under following conditions of dry gas flow rate: 10 L/min; nebulizer pressure: 60 psi; dry gas temperature: 350° C.; capillary voltage: 3500 v; and m/z scan range: 100-1200; and
(2) HPLC-MS$^n$ is carried out through the negative ion detection under following conditions of dry gas flow rate: 10 L/in; nebulizer pressure: 60 psi; dry gas temperature: 350° C.; capillary voltage: 3500 v; m/z scan range: 100-800; and fragment amplitude: 1.5-3.0 v.

4. The preparation according to claim 1, characterized in that it comprises the components having a quasi-molecular ion mass peak m/z of 931, 945, 799, 1107, 769, 769, 783, 637, 637, 945, 945, 781, 751, 751, 765, 783, 783, 765, and 765[M-H]$^-$ respectively, wherein:
the component with 931 [M-H]$^-$ has a fragment ion m/z of 799[M-H-Xyl]$^-$, 637[M-H-Xyl-Glc]$^-$, and 475[M-H-Xyl-2Glc]$^-$;
the component with 945 [M-H]$^-$ has a fragment ion m/z of 799[M-H-Rham]$^-$, 783[M-H-Glc]$^-$, 637[M-H-Rham-Glc]$^-$, and 475[M-H-Rham-2Glc]$^-$;
the component with 799 [M-H]$^-$has a fragment ion m/z of 637[M-H-Glc]$^-$, and 475[M-H-2Glc]$^-$;
the component with 1107 [M-H]$^-$ has a fragment ion m/z of 945 [M-H-Glc]$^-$, 783[M-H-2Glc]$^-$, 621 [M-H-3Glc]$^-$, and 459[M-H-4Glc]$^-$;
the component with 769 [M-H]$^-$ has a fragment ion m/z of 637[M-H-Xyl]$^-$, and 475[M-H-Xyl-Glc]$^-$;
the component with 769 [M-H]$^-$ has a fragment ion m/z of 637[M-H-Xyl]$^-$, and 475 [M-H-Xyl-Glc]$^-$;
the component with 783 [M-H]$^-$ has a fragment ion m/z of 637[M-H-Rham]$^-$, and 475[M-H-Rham-Glc]$^-$;
the component with 637 [M-H]$^-$ has a fragment ion m/z of 475[M-H-Glc]$^-$;

the component with 637 [M-H]⁻ has a fragment ion m/z of 475[M-H-Glc]⁻;
the component with 945 [M-H]⁻ has a fragment ion m/z of 783[M-H-Glc]⁻, 621 [M-H-2Glc]⁻, and 459[M-H-3Glc]⁻;
the component with 945 [M-H]⁻ has a fragment ion m/z of 783[M-H-Glc]⁻, 621 [M-H-2Glc]⁻, and 459[M-H-3Glc]⁻;
the component with 781 [M-H]⁻ has a fragment ion m/z of 619[M-H-Glc]⁻, and 457[M-H-2Glc]⁻;
the component with 751 [M-H]⁻ has a fragment ion m/z of 619[M-H-Xyl]⁻;
the component with 751 [M-H]⁻ has a fragment ion m/z of 619[M-H-Xyl]⁻;
the component with 765 [M-H]⁻ has a fragment ion m/z of 619[M-H-Rham]⁻, and 457[M-H-Rham-Glc]⁻;
the component with 783 [M-H]⁻ has a fragment ion m/z of 621[M-H-Glc]⁻, and 459[M-H-2Glc]⁻;
the component with 783 [M-H]⁻ has a fragment ion m/z of 621[M-H-Glc]⁻, and 459[M-H-2Glc]⁻;
the component with 765 [M-H]⁻ has a fragment ion m/z of 603[M-H-Glc]⁻, and 441[M-H-2Glc]⁻;
the component with 765 [M-H]⁻ has a fragment ion m/z of 603[M-H-Glc]⁻, and 441[M-H-2Glc]⁻;
wherein the mass spectrum analysis is carried out as follows:
(1) HPLC-MS is carried out through the negative ion detection under following conditions of dry gas flow rate: 10 L/min; nebulizer pressure: 60 psi; dry gas temperature: 350° C.; capillary voltage: 3500 v; and m/z scan range: 400-1500; and
(2) HPLC-MS″ is carried out through the negative ion detection under following conditions of dry gas flow rate: 10 L/min; nebulizer pressure: 60 psi; dry gas temperature: 350° C.; capillary voltage: 3500 v; m/z scan range: 400-1200; and fragment amplitude: 1.2-1.5 v.

5. The preparation according to claim 1, characterized in that it comprises the components having a quasi-molecular ion mass peak m/z of 417, 717, 359, 717, 339, and 493 [M-H]⁻ respectively, wherein
the component with 417 [M-H]⁻ has a second fragment ion m/z of 175[M-CO₂-R-H₂O]⁻ and 373[M-H-CO₂]⁻, and a third fragment ion m/z of 147, 157 and 133;
the component with 717 [M-H]⁻ has a second fragment ion m/z of 519[M-R-H₂O]⁻ and 321[M-2R-2H₂O]⁻, a third fragment ion m/z of 321[M-R-H₂O]⁻ and 339[M-R]⁻, and a third fragment ion m/z of 279, 293, 249, 223 and 185;
the component with 359 [M-H]⁻ has a second fragment ion m/z of 161[M-R-H₂O]⁻, 179[M-R]⁻, and 195;
the component with 717 [M-H]⁻ has a second fragment ion m/z of 519[M-R-H₂O]⁻ and 321[M-2R-2H₂O]⁻, a third fragment ion m/z of 321[M-R-H₂O]⁻ and 339[M-R]⁻, and a forth fragment ion m/z of 279, 293, 249, 233 and 185;
the component with 339 [M-H]⁻ has a second fragment ion m/z of 321[M-H-H₂O]⁻ and 295[M-H-CO₂]⁻, a third fragment ion m/z of 279 and 267, and a forth fragment ion m/z of 251; and
the component with 493 [M-H]⁻ has a second fragment ion m/z of 295[M-R-H₂O]⁻, and a third fragment ion m/z of 159 and 109;
wherein the mass spectrum analysis is carried out as follows:
(1) HPLC-MS is carried out through the negative ion detection under following conditions of dry gas flow rate: 10 L/min; nebulizer pressure: 60 psi; dry gas temperature: 350° C.; capillary voltage: 3500 v; and m/z scan range: 100-1200; and
(2) HPLC-MS″ is carried out through the negative ion detection under following conditions of dry gas flow rate: 10 L/min; nebulizer pressure: 60 psi; dry gas temperature: 350° C.; capillary voltage: 3500 v; m/z scan range: 100-800; and fragment amplitude: 1.5-3.0 v; said preparation further comprises the components having a quasi-molecular ion mass peak m/z of 931, 945, 799, 1107, 769, 769, 783, 637, 637, 945, 945, 781, 751, 751, 765, 783, 783, 765, and 765 [M-H]⁻, wherein:
the component with 931 [M-H]⁻ has a fragment ion m/z of 799[M-H-Xyl]⁻, 637[M-H-Xyl-Glc]⁻, and 475 [M-H-Xyl-2Glc]⁻;
the component with 945 [M-H]⁻ has a fragment ion m/z of 799[M-H-Rham]⁻, 783 [M-H-Glc]⁻, 637[M-H-Rham-Glc]⁻, and 475 [M-H-Rham-2Glc]⁻;
the component with 799 [M-H]⁻ has a fragment ion m/z of 637[M-H-Glc]⁻, and 475 [M-H-2Glc]⁻;
the component with 1107 [M-H]⁻ has a fragment ion m/z of 945 [M-H-Glc]⁻, 783 [M-H-2Glc]⁻, 621[M-H-3Glc]⁻, and 459[M-H-4Glc]⁻;
the component with 769 [M-H]⁻ has a fragment ion m/z of 637[M-H-Xyl]⁻, and 475[M-H-Xyl-Glc]⁻;
the component with 769 [M-H]⁻ has a fragment ion m/z of 637[M-H-Xyl]⁻, and 475[M-H-Xyl-Glc]⁻;
the component with 783 [M-H]⁻ has a fragment ion m/z of 637[M-H-Rham]⁻, and 475[M-H-Rham-Glc]⁻;
the component with 637 [M-H]⁻ has a fragment ion m/z of 475[M-H-Glc]⁻;
the component with 637 [M-H]⁻ has a fragment ion m/z of 475[M-H-Glc]⁻;
the component with 945 [M-H]⁻ has a fragment ion m/z of 783[M-H-Glc]⁻, 621 [M-H-2Glc]⁻, and 459[M-H-3Glc]⁻;
the component with 945 [M-H]⁻ has a fragment ion m/z of 783 [M-H-Glc]⁻, 621 [M-H-2Glc]⁻, and 459[M-H-3Glc]⁻;
the component with 781 [M-H]⁻ has a fragment ion m/z of 619[M-H-Glc]⁻, and 457[M-H-2Glc]⁻;
the component with 751 [M-H]⁻ has a fragment ion m/z of 619[M-H-Xyl]⁻;
the component with 751 [M-H]⁻ has a fragment ion mz of 619[M-H-Xyl]⁻;
the component with 765 [M-H]⁻ has a fragment ion m/z of 619[M-H-Rham]⁻, and 457[M-H-Rham-Glc]⁻;
the component with 783 [M-H]⁻ has a fragment ion m/z of 621[M-H-Glc]⁻, and 459[M-H-2Glc]⁻;
the component with 783 [M-H]⁻ has a fragment ion m/z of 621 [M-H-Glc]⁻, and 459[M-H-2Glc]⁻;
the component with 765 [M-H]⁻ has a fragment ion m/z of 603 [M-H-Glc]⁻, and 441 [M-H-2Glc]⁻;
the component with 765 [M-H]⁻ has a fragment ion m/z of 603[M-H-Glc]⁻, and 441[M-H-2Glc]⁻;
wherein the mass spectrum analysis is carried out as follows:
(1) HPLC-MS is carried out through the negative ion detection under following conditions of dry gas flow rate: 10 L/min; nebulizer pressure: 60 psi; dry gas temperature: 350° C.; capillary voltage: 3500 v; and m/z scan range: 400-1500; and
(2) HPLC-MS″ is carried out through the negative ion detection under following conditions of dry gas flow rate: 10 L/min; nebulizer pressure: 60 psi; dry gas temperature: 350° C.; capillary voltage: 3500 v; m/z scan range: 400-1200; and fragment amplitude: 1.2-1.5 v.

6. The preparation according to claim 5, characterized in that it comprises Salvianolic acid D, Salvianolic acid B, Rosmarinic acid, Salvianolic acid B, Salvianolic acid G, Salvianolic acid A, Danshensu, Protocatechualdehyde, Isolithospermic acid A, Isolithospermic acid B, Tanshinone I, Tanshinone hA, Notoginsenoside $R_1$, Ginsenoside Re, Ginsenoside $Rg_1$, Ginsenoside Rb1, Notoginsenoside R2, Notoginsenoside R2 iso., Ginsenoside Rg2, Ginsenoside Rh1, Ginsenoside Rh1 iso., Ginsenoside Rd, Ginsenoside Rd iso., Ginsenoside Rf-H2O, Notoginsenoside R2-H2O, Ginsenoside Rg6 or F4, Ginsenoside 20(R)-Rg3, Ginsenoside 20(S)-Rg3, Ginsenoside Rk1, Ginsenoside Rg5, Ginsenoside Rk3, and Ginsenoside Rh4.

7. The preparation according to claim 1, characterized in that it has the physical and chemical parameters characterized as follows:

in the HPLC spectrum, there are 8 peaks which have a ratio of single peak area to total peak area greater than 2%; the average retention time of these 8 peaks is 6.04, 9.90, 16.89, 17.84, 20.31, 23.74, 27.73, and 31.02, respectively, the RSD % of the retention time is 0.31, 0.25, 0.61, 0.70, 0.96, 0.76, 0.50, and 1.18, respectively; the average peak area is 1627.92, 2575.54. 366.89, 381.40, 186.08, 555.35, 281.91, and 1852.33, respectively, the RSD % of the peak area is 5.91, 13.53, 10.92, 13.81, 12.04, 10.48, 18.08, and 14.84, respectively; and the ratio of single peak area to total peak area accounts for 19.6%-22.0%, 28.5-37.4%, 4.2%-5.2%, 4.2%-5.5%, 2.1%-2.7%, 6.4%-7.8%, 3.0%-4.3%, and 20.2%-27.2%, respectively;

wherein the above physical and chemical parameters are determined under the following conditions:

(1) high performance liquid chromatography: filler: octadecylsilyl-silica gel; flow rate: 1.000 ml/min; and detection wavelength: 280 nm; and (2) elution: mobile phase A: 0.02% aqueous phosphoric acid solution; mobile phase B: 80% acetonitrile-0.02% aqueous phosphoric acid solution; and gradient elution: mobile phase A being changed from 90% to 78% homogeneously and mobile phase B being changed from 10% to 22% homogeneously during 0 to 8 min, mobile phase A from 78% to 74% and mobile phase B from 22% to 26% during 8 to 15 min, and mobile phase A from 74% to 48% and mobile phase B from 26% to 52% during 15 to 55 min;

and wherein the sample solution is prepared and determined through the following steps of: weighing 10 pills of the preparations accurately and adding them into a 10 ml measuring bottle; adding distilled water at an amount sufficient to dissolve the preparations through shaking with ultrasound for 15 minutes; adding more distilled water to achieve a volume of 10 ml; subjecting the resultant solution to centrifugation or filtration to obtain the sample solution; injecting an accurate 10 µl of the sample solution into the HPLC system; and determining the sample solution in accordance with HPLC chromatography to obtain the HPLC spectrum.

8. The preparation according to claim 7, characterized in that the 8 peaks with average retention time of 6.04, 9.90, 16.89, 17.84, 20.31, 23.74, 27.73 and 31.02 correspond with Danshensu, Protocatechualdehyde, Isolithospermic acid A, Isolithospermic acid B, Salvianolic acid D, Rosmarinic acid, Salvianolic acid B, and Salvianolic acid A, respectively.

9. A process for preparing the preparation according to claim 1, comprising:

weighing *Radix Salviae Miltiorrhizae* and *Radix Notoginseng*;

adding sodium hydroxide, sodium bicarbonate, sodium carbonate, potassium hydroxide, potassium bicarbonate, potassium carbonate or a mixture thereof in an amount of 0.5%-4.0% based on the total weight of said medicinal materials;

boiling the resulting mixture out in 3-6 folds of water for 2-4 times;

subjecting the mixture to filtration and concentrating the combined filtrates;

adding an ethanol with the concentration above 70% in an amount sufficient to achieve a 65-70% content of the ethanol;

allowing the mixture to stand and separating the supernatant;

recovering the ethanol from the supernatant, and concentrating the residue until it has a relative density of 1.20-1.50, which is an extract of *Radix Salviae Miltiorrhizae-Radix Notoginseng*;

mixing the above extract with Borneo 1 or an oil of *Lignum Dalbergiae Odorferae*; and adding an excipient to obtain the preparation.

10. The process for preparing the preparation according to claim 9, characterized in that said excipient is starch, dextrin, lactose, microcrystalline cellulose, hydroxypropyl methyl cellulose, polyethylene glycol, magnesium stearate, micro silicon gel, xylitol, lactitol, glucose, glycine, mannitol, methyl starch sodium, cross-linked sodium carboxyl methyl cellulose, cross-linked polyvinylpyrrolidone as such or in the water, or a mixture of more than one of the above adjutants; said preparation is in the dosage form of injection, tablet, sustained-release tablet, drop pill, granule, injection powder, capsule, microgranule, or oral disintegrant.

11. The process for preparing the preparation according to claim 10, characterized in that said preparation is in the dosage form of drop pill.

12. The process for preparing the preparation according to claim 11, characterized in that it comprises the steps of:

weighing *Radix Salviae Miltiorrhizae* and *Radix Notoginseng*;

adding sodium bicarbonate in an amount of 1.4%-1.9% based on the total weight of said medicinal materials;

boiling the resulting mixture out in 4-5 folds of water for 2-3 hours, and then in 3-4 folds of water for 1-2 hours;

subjecting the mixture to filtration and concentrating the combined filtrates until a specific gravity of 1.16-1.20 is achieved;

adding an ethanol with the concentration above 70% in an amount sufficient to obtain a 65-70% content of the ethanol;

allowing the mixture to stand for 8-12 hours and separating the supernatant;

recovering the ethanol from the supernatant, and concentrating the residue until it has a relative density of 1.32-1.40, which is an extract of *Radix Salviae Miltiorrliizae-Radix Notoginseng*;

mixing the above extract with Borneol or an oil of *Lignum Dalbergiae Odorzferae*, and polyethylene glycol-6000 uniformly;

heating the mixture to melting;

dropping the melt into a coolant of liquid paraffin or methyl silicone oil through a drop-pill machine;

taking out the obtained drop pills and subjecting them to an oil removal; and sieving the pills to obtain the desired preparation.

* * * * *